(12) United States Patent
Takai

(10) Patent No.: US 11,115,577 B2
(45) Date of Patent: Sep. 7, 2021

(54) DRIVER MONITORING DEVICE MOUNTING STRUCTURE

(71) Applicant: TOYOTA JIDOSHA KABUSHIKI KAISHA, Toyota (JP)

(72) Inventor: Yusuke Takai, Chiryu (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/591,886

(22) Filed: Oct. 3, 2019

(65) Prior Publication Data

US 2020/0155075 A1 May 21, 2020

(30) Foreign Application Priority Data

Nov. 19, 2018 (JP) .............................. JP2018-216683

(51) Int. Cl.
| | | |
|---|---|---|
| *H04N 5/225* | (2006.01) | |
| *A61B 5/00* | (2006.01) | |
| *B60R 16/023* | (2006.01) | |
| *B60R 11/04* | (2006.01) | |
| *G06K 9/00* | (2006.01) | |
| *B60R 11/00* | (2006.01) | |
| *A61B 5/18* | (2006.01) | |

(52) U.S. Cl.
CPC ......... *H04N 5/2257* (2013.01); *A61B 5/6893* (2013.01); *B60R 11/04* (2013.01); *B60R 16/023* (2013.01); *G06K 9/00845* (2013.01); *H04N 5/2253* (2013.01); *A61B 5/0077* (2013.01); *A61B 5/18* (2013.01); *B60R 2011/001* (2013.01)

(58) Field of Classification Search
CPC . B60R 16/023; B60R 11/04; B60R 2011/001; H04N 5/2253; H04N 5/2257; G06K 9/00845; A61B 5/18; A61B 5/0077; A61B 5/6893
USPC ......................................................... 348/373
See application file for complete search history.

(56) References Cited

U.S. PATENT DOCUMENTS

| | | | | |
|---|---|---|---|---|
| 7,777,778 B2* | 8/2010 | Scharenbroch | .... | G06K 9/00845 348/78 |
| 8,052,338 B2* | 11/2011 | Usami | ..................... | B60R 11/04 396/419 |
| 8,233,046 B2* | 7/2012 | Ohue | ..................... | B60R 11/04 348/148 |
| 8,435,188 B2* | 5/2013 | Ohue | ....................... | A61B 5/18 600/558 |

(Continued)

FOREIGN PATENT DOCUMENTS

| | | |
|---|---|---|
| JP | 2007-069680 A | 3/2007 |
| JP | 2007-069681 A | 3/2007 |

(Continued)

*Primary Examiner* — Pritham D Prabhakher
(74) *Attorney, Agent, or Firm* — Sughrue Mion, PLLC

(57) ABSTRACT

A driver monitoring device mounting structure that includes: a driver monitoring device main body that is attached to a steering column; a supporting component that has an anchoring portion and a fastening portion, and that supports a connector that is attached to a lead wire that is drawn out from the driver monitoring device main body; and a column cover that has a temporary fixing portion to which the anchoring portion is temporarily fixed, and a fixing portion to which the fastening portion is fixed, and that covers the steering column.

5 Claims, 6 Drawing Sheets

(56) References Cited

U.S. PATENT DOCUMENTS

| | | | |
|---|---|---|---|
| 8,457,364 B2* | 6/2013 | Hiroshi | A61B 5/0077 |
| | | | 382/117 |
| D751,437 S * | 3/2016 | Lisseman | D10/104.1 |
| 10,293,758 B2* | 5/2019 | Lowell | B60R 11/0241 |
| 10,614,328 B2* | 4/2020 | Lisseman | H04N 7/18 |
| 10,787,189 B2* | 9/2020 | Lisseman | B60W 10/20 |
| 2009/0115846 A1 | 5/2009 | Ohue et al. | |
| 2010/0002075 A1* | 1/2010 | Jung | B60K 28/06 |
| | | | 348/78 |
| 2010/0218641 A1* | 9/2010 | Neumann | B62D 1/046 |
| | | | 74/552 |
| 2010/0260495 A1 | 10/2010 | Usami et al. | |
| 2011/0025836 A1 | 2/2011 | Tamaki et al. | |
| 2012/0169503 A1* | 7/2012 | Wu | G08B 21/06 |
| | | | 340/575 |
| 2013/0120574 A1* | 5/2013 | Omi | G08B 21/06 |
| | | | 348/148 |
| 2014/0313333 A1* | 10/2014 | Le | B60R 16/0231 |
| | | | 348/148 |
| 2016/0188987 A1* | 6/2016 | Lisseman | G06K 9/00845 |
| | | | 348/148 |
| 2016/0191859 A1* | 6/2016 | Lisseman | B60K 35/00 |
| | | | 348/148 |
| 2018/0118131 A1* | 5/2018 | Lowell | B60R 11/0241 |
| 2018/0319407 A1* | 11/2018 | Lisseman | B60W 50/0098 |
| 2019/0135325 A1* | 5/2019 | Lisseman | H04N 5/247 |

FOREIGN PATENT DOCUMENTS

| | | |
|---|---|---|
| JP | 2009-154708 A | 7/2009 |
| JP | 2011-154721 A | 8/2011 |
| JP | 2012-111274 A | 6/2012 |

* cited by examiner

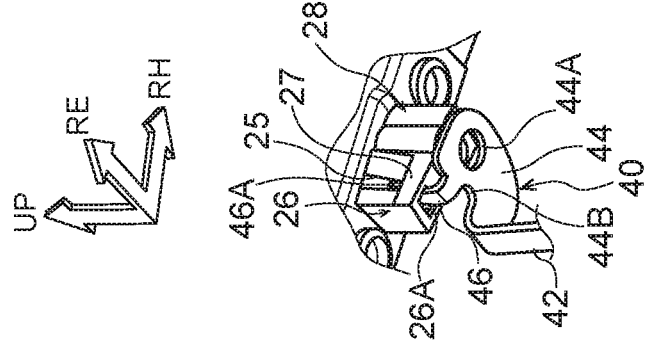

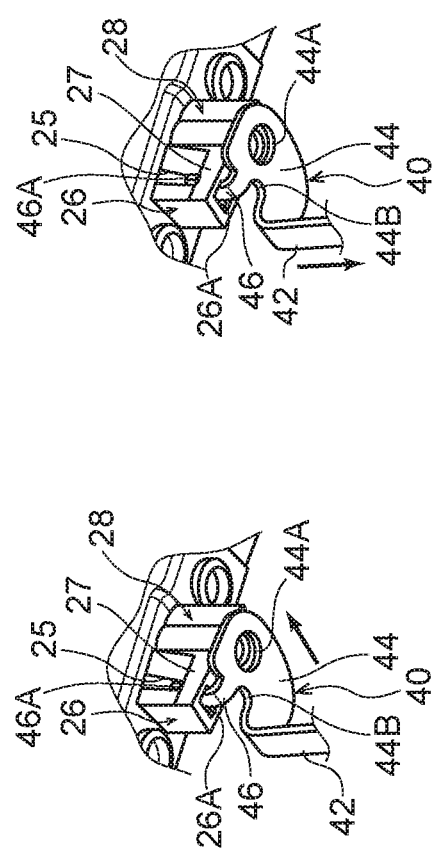

DRIVER MONITORING DEVICE MOUNTING STRUCTURE

CROSS-REFERENCE TO RELATED APPLICATION

This application is based on and claims priority under 35 USC 119 from Japanese Patent Application No. 2018-216683 filed on Nov. 19, 2018, the disclosure of which is incorporated by reference herein.

BACKGROUND

Technical Field

The present disclosure relates to a mounting structure for a driver monitoring device.

Related Art

In order to monitor the orientation of the face of a driver while this driver is driving a vehicle (for example, to check whether the driver is distracted or is becoming drowsy), a structure exists in which a driver monitoring camera is provided in an upper portion of a steering column (see, for example, Japanese Unexamined Patent Application (JP-A) No. 2011-154721).

Normally, various types of meters are disposed within the line of sight of a driver. Accordingly, if a driver monitoring camera (i.e., a driver monitoring device main body) is mounted on an upper portion of a steering column, in order to ensure that visibility of these various meters by the driver is maintained, it is desired that this driver monitoring camera be made as small as possible.

One proposal for reducing the size of this camera is a structure in which a lead wire used to output a video signal is drawn out from the camera. More specifically, in order to connect together a video signal input connector that is provided on a vehicle side, and a video signal output connector that is provided on the camera side, a structure may be considered in which a lead wire is drawn out from the camera, and a connector is attached to a distal end of that lead wire.

If a structure such as this is employed, then in order to simply the task of connecting together the video signal input connector and the video signal output connector, it is necessary for the connector that is attached to the distal end of the lead wire to be fixed via a bracket (i.e., a supporting component) to a fixing portion of a column cover that covers the steering column.

However, because the lead wire for the video signal output has an internal metal shielding component for reducing noise, the lead wire is extremely rigid (i.e., stiff), and when curving the lead wire in order to lead it to the fixing portion of the column cover, it is difficult to stabilize the position of the bracket because of the reaction force from the lead wire. In other words, it is difficult to fix the bracket onto the fixing portion or the like of the column cover.

SUMMARY

An aspect of the disclosure is a driver monitoring device mounting structure. The structure includes: a driver monitoring device main body that is attached to a steering column; a supporting component that has an anchoring portion and a fastening portion, and that supports a connector that is attached to a lead wire that is drawn out from the driver monitoring device main body; and a column cover that has a temporary fixing portion to which the anchoring portion is temporarily fixed, and a fixing portion to which the fastening portion is fixed, and that covers the steering column.

BRIEF DESCRIPTION OF THE DRAWINGS

Exemplary embodiments of the present disclosure will be described in detail based on the following figures, wherein:

FIGS. 5A-5E are perspective views as seen from a lower side showing a mounting procedure for the bracket according to the present exemplary embodiment.

DETAILED DESCRIPTION

Hereinafter, an exemplary embodiment for implementing the present disclosure will be described in detail with reference to the drawings. Note that an arrow UP, an arrow RE, and an arrow RH that are shown in the appropriate drawings respectively indicate a vehicle upward direction, a vehicle rearward direction, and a right side in a vehicle width direction. Accordingly, if front-rear, left-right, or up-down directions are used in the following description, then, unless specifically stated otherwise, these refer respectively to the front-rear directions of the vehicle, the left-right directions of the vehicle (i.e., the vehicle width direction), and the up-down directions of the vehicle.

Figure 1:
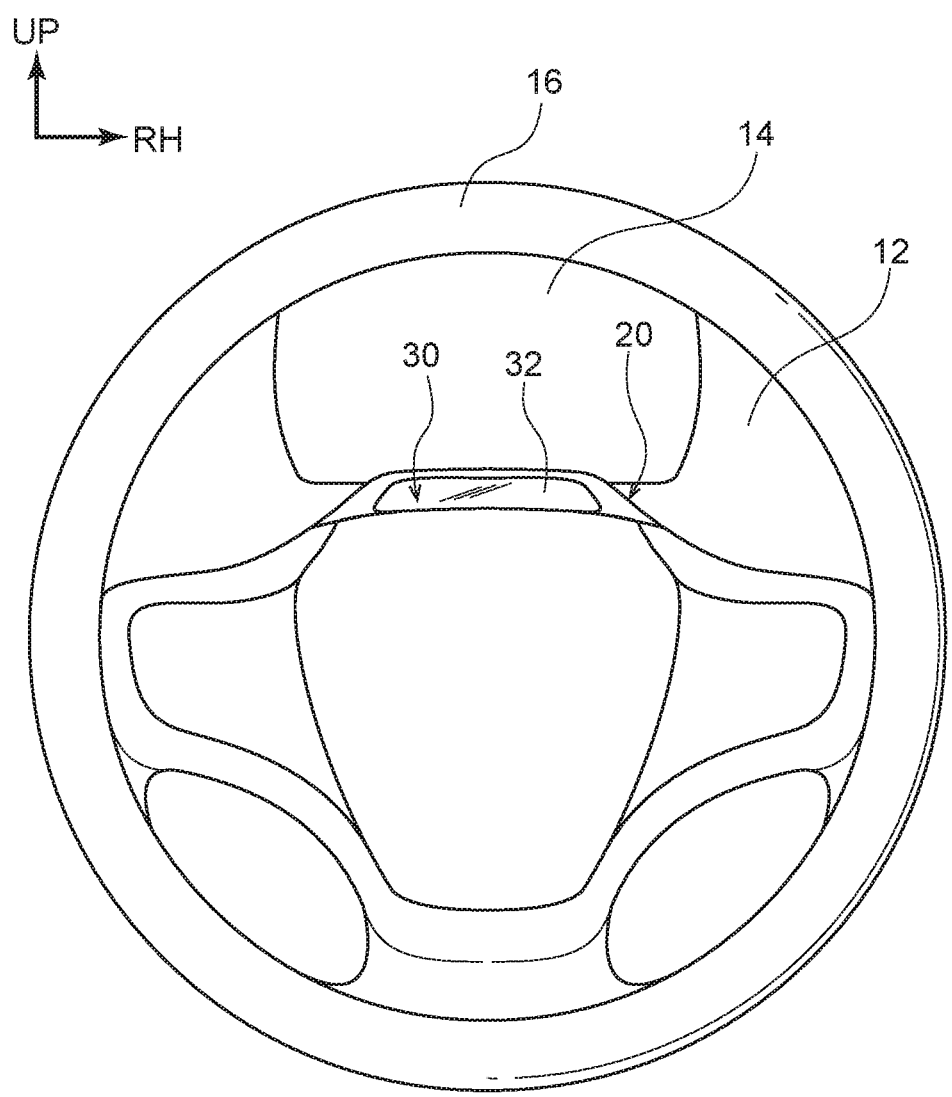
FIG. 1 is a front view showing a driver monitoring camera according to an exemplary embodiment.
Figure 2:
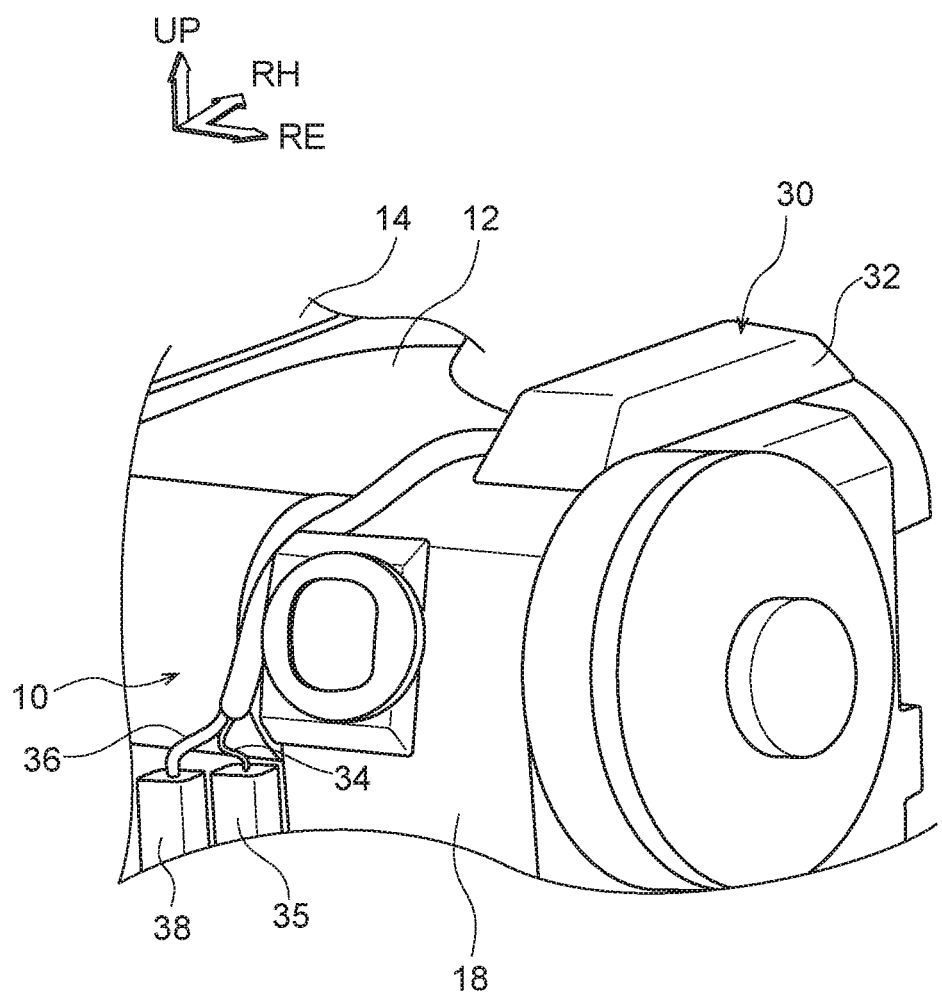
FIG. 2 is a perspective view as seen from a rear side showing a lead wire leading from a camera main body of the driver monitoring camera according to the present embodiment.
Figure 3:
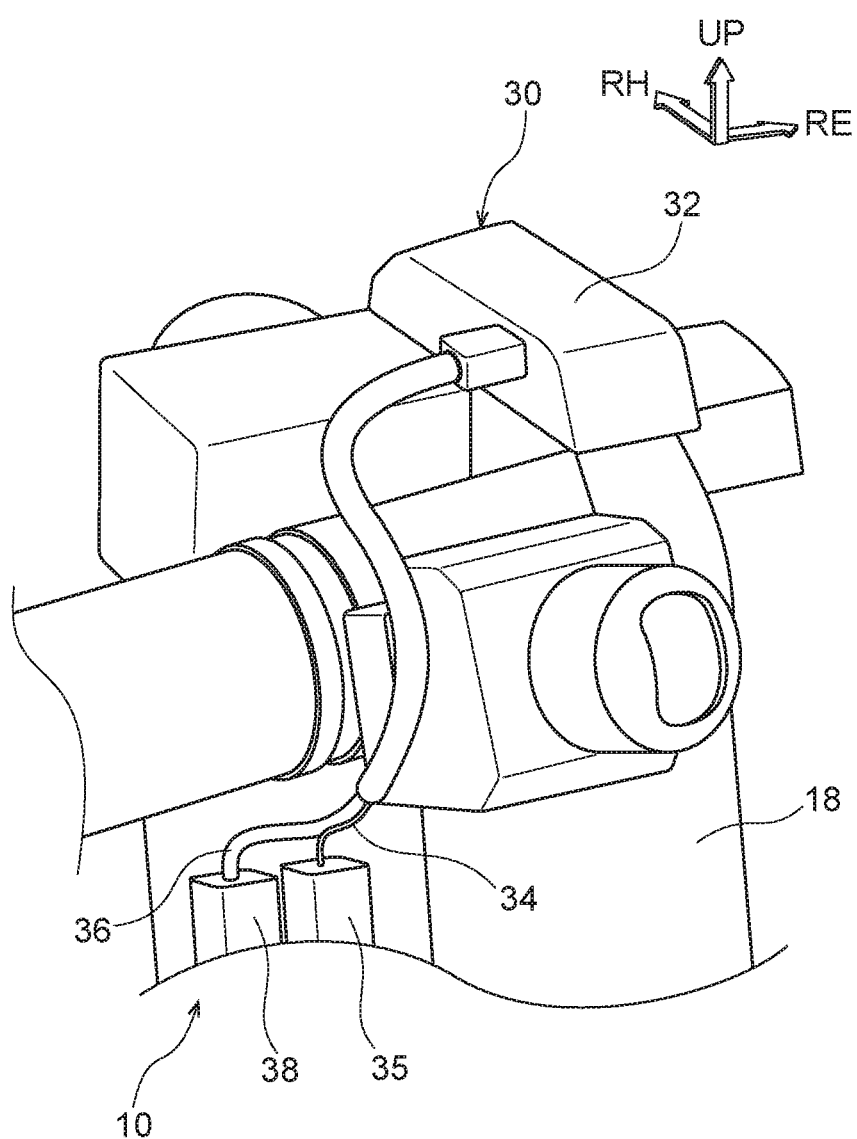
FIG. 3 is a perspective view as seen from a front side showing the lead wire leading from the camera main body of the driver monitoring camera according to the present embodiment.

As is shown in FIG. 1 through FIG. 3, a display unit 14 on which various meter instruments such as a speedometer and the like are displayed is disposed in an instrument panel 12 on a vehicle front side of a steering wheel 16. In addition, a camera main body 32 of a driver monitoring camera (hereinafter, referred to simply as a 'camera') 30, which is serving as a driver monitoring device, is mounted in an upper portion of a steering column 18.

A column cover 20 (see FIG. 4) is also provided on the steering column 18. The column cover 20 is formed substantially in a U-shape whose open side is on the front side when looked at in plan view, and has a main body portion 22 that covers the steering column 18 from the upper side, and a pair of left and right side portions 24 that extend towards the front side from both end portions in the vehicle width direction of a front end portion 22B of the main body portion 22. Additionally, an aperture portion 22A that enables a lens of the camera main body 32 to be directed towards the driver is formed in a rear end portion of the main body portion 22.

A temporary fixing portion 26 that enables a bracket 40 which is used to fix a connector (described below) to be temporarily fixed in position, and a fixing portion 28 that enables this bracket 40 to be permanently fixed in position are formed as a single integrated unit on one side in the vehicle width direction (for example, on the left side) of the front end portion 22B of the main body portion 22. Note that the temporary fixing portion 26 is disposed on the left side of the fixing portion 28. Note also that the temporary fixing portion 26 and the fixing portion 28 of the column cover 20 forming the mounting structure 10 according to the present exemplary embodiment are described below in detail together with the bracket 40.

As is shown in FIG. 1, the camera main body 32, which is serving as the driver monitoring device main body forming the mounting structure 10 according to the present exemplary embodiment, is formed having a low height and an extended width in the vehicle width direction (in other words, is formed in a substantially flattened shape) in order to maintain the drivers ability to view the display unit 14. In addition, as is shown in FIG. 2 and FIG. 3, in order to reduce the size of the camera main body 32, a lead wire 36, which is used to output a video signal, together with a lead wire 34, which is used to supply power, lead out from the camera main body 32.

Note that the camera 30 is formed by the camera main body 32 and the lead wires 34 and 36. In addition, because the video signal output lead wire 36 has an internal (i.e., on an inner circumferential wall side of the lead wire 36) metal shielding component that is used to reduce noise, the lead wire 36 is thicker (i.e., has a larger outer diameter), and also has a greater rigidity (i.e., is stiffer) than the power supply lead wire 34. As a result, it is possible to distinguish between the video signal output lead wire 36 and the power supply lead wire 34.

Moreover, due to the restraints imposed by peripheral parts of the camera main body 32 in the steering column 18, the lead wire 34 and the lead wire 36 are laid across the outer shape of the steering column 18 and then turn in a downwards direction. In other words, the lead wire 34 and the lead wire 36 are laid so that they curve in conformity with the outer shape of the steering column 18.

Figure 4:
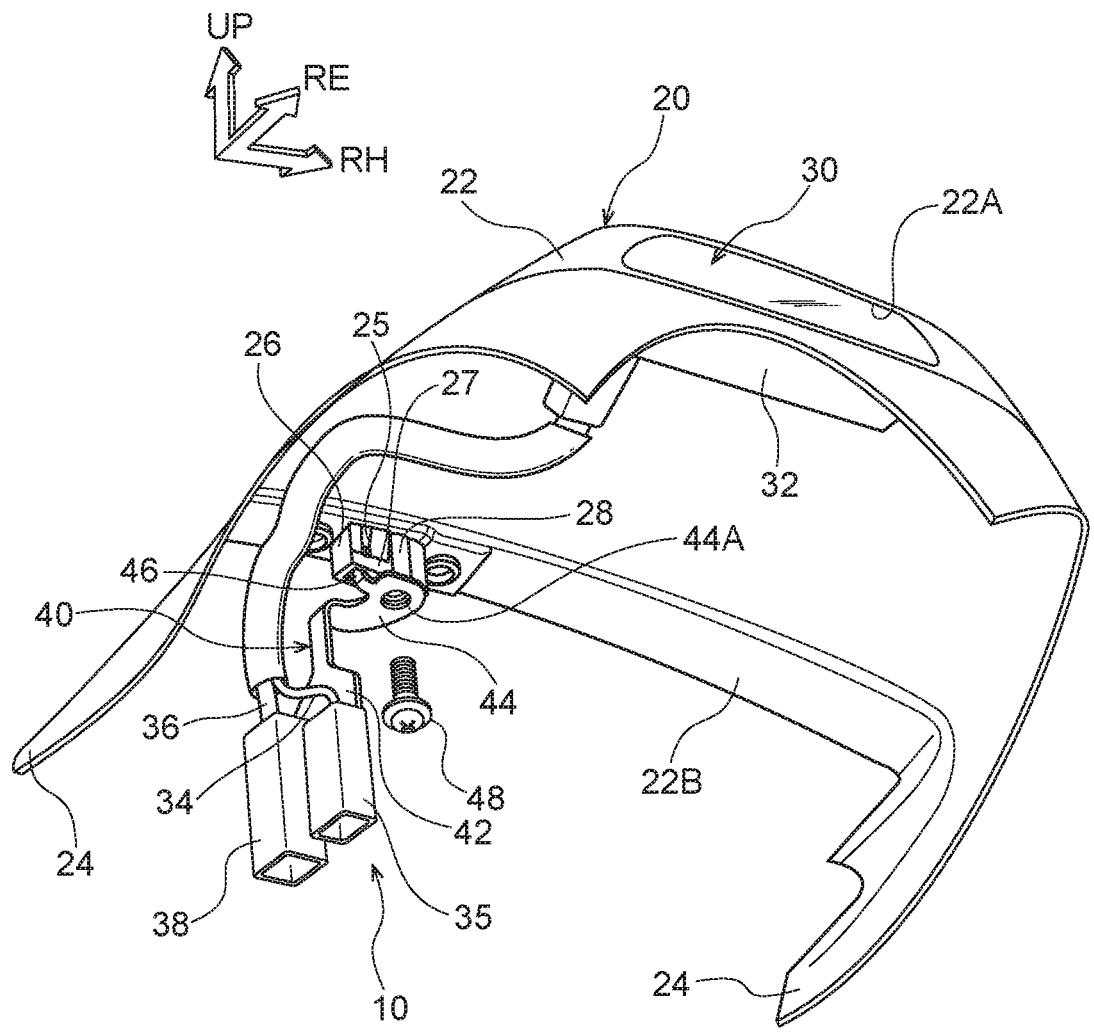
FIG. 4 is a perspective view as seen from a lower side showing a mounting structure of a bracket according to the present exemplary embodiment.

Moreover, as is shown in FIG. 2 through FIG. 4, a connector 35 to which a connector that is used for supplying power from the vehicle is connected is attached to a distal end of the power supply lead wire 34. In addition, a connector 38 to which a connector that is used to input video signals to the vehicle is connected is attached to a distal end of the video signal output lead wire 36.

As is shown in FIG. 4, the connector 35 and the connector 38 are both formed in a square cylinder shape, and a portion of an outer wall of each connector is supported on the bracket 40 that is serving as a supporting component forming part of the mounting structure 10 according to the present exemplary embodiment. The bracket 40 has a flat-plate shaped holding portion 42 to which a portion of an outer wall each of the connector 35 and the connector 38 is attached, a flat-plate shaped fastening portion 44 that continues on from the holding portion 42 and is fixed in place by being fastened to the fixing portion 28 of the column cover 20, and a flat-plate shaped hook 46 that is serving as a temporary fixing portion and is temporarily fixed to the temporary fixing portion 26 of the column cover 20.

Note that as is shown in FIG. 5A, an upper end portion 46A, which is a distal end of the hook 46, is bent towards the rear side. A normal direction of the fastening portion 44 extends in an up-down direction, and a through hole 44A through which is inserted a fixing screw 48 (see FIG. 4) that fixes the bracket 40 in place when screwed in is formed in the fastening portion 44. Normal directions of the holding portion 42 and the hook 46 extend in the vehicle width direction.

In other words, the holding portion 42, which is made to extend towards the lower side by being bent substantially perpendicularly downwards from a front side of an end portion 44B on one side (i.e., on the left side) in the vehicle width direction of the fastening portion 44, is formed integrally with the fastening portion 44. Moreover, the hook 46, which is made to extend towards the upper side by being bent substantially perpendicularly upwards from a rear side of the end portion 44B of the fastening portion 44, is also formed integrally with the fastening portion 44.

In addition, the temporary fixing portion 26 and the fixing portion 28 of the column cover 20 are also formed integrally with each other, so that their overall integrated shape is substantially in the form of a rectangular parallelepiped. A female threaded portion 28A into which the fixing screw 48 (see FIG. 4) is screwed from a bottom wall 28B side is formed in the fixing portion 28. An aperture portion 26A through which the hook 46 is able to be inserted is formed in a bottom wall 26B of the temporary fixing portion 26.

A slit portion 25 through which an upper end portion 46A of the hook 46, once this has been inserted into the aperture portion 26A, can be inserted so as to protrude towards the rear is formed in a rear wall 26C of the temporary holding portion 26. Additionally, a catch portion 27 that catches the upper end portion 46A of the hook 46, after this has been inserted through the slit portion 25, is formed in a lower end portion of the rear wall 26C of the temporary fixing portion 26.

Next, a description will be given of an operation performed in the mounting structure 10 according to the present exemplary embodiment having the above-described structure.

The bracket 40 supporting the connectors 35 and 38 that are attached to the distal ends of the lead wires 34 and 36 is temporarily fixed in the manner described below to the temporary fixing portion 26 of the column cover 20, and is then fixed in place by being fastened to the fixing portion 28. In other words, as is shown in FIG. 5A and FIG. 5B, firstly, an operator grasps the bracket 40 with their fingers, and then inserts the hook 46 thereof through the aperture portion 26A in the temporary holding portion 26.

Next, as is shown in FIG. 5C, after the hook 46 has been inserted far enough into the aperture portion 26A that the fastening portion 44 of the bracket 40 is adjacent to (or abutting against) the bottom wall 28B of the fixing portion 28, then as is shown in FIG. 5D, the fastening portion 44 (i.e., the bracket 40) is made to slide towards the rear. As a result of this, the upper end portion 46A of the hook 46 is inserted into the slit portion 25.

If, in this state, the operator then removes their finger, the fastening portion 44 of the bracket 40 is urged towards the lower side by reaction force from the lead wire 36. In other words, because the metal shielding component is provided inside the lead wire 36, the lead wire 36 is extremely rigid (i.e. stiff). Because of this, if the lead wire 36 is drawn out while being curved, reaction force against this curved state is generated in the lead wire 36.

Accordingly, as is shown in FIG. 5E, the upper end portion 46A of the hook 46 is fully caught by the catch portion 27 provided on the lower end portion of the slit portion 25 due to the reaction force generated by the lead wire 36 (i.e., is anchored so as to withstand the reaction force generated by the lead wire 36). Note that, at this time, a slight gap is formed between the bottom wall 28B of the fixing portion 28 and the fastening portion 44. In this state, the fixing screw 48 shown in FIG. 4 is inserted into the through hole 44A in the fastening portion 44, and is screwed into the female threaded portion 28A formed in the fixing portion 28. As a result, the fastening portion 44 of the bracket 40 is fixed to the fixing portion 28.

In this way, once the hook 46 has been temporarily fixed to the temporary fixing portion 26 (i.e., once the upper end portion 46A of the hook 436 has been caught by the catch portion 27), the fastening portion 44 of the bracket 40 supporting the connectors 35 and 38 that are attached to the distal ends of the leads 34 and 36 which have been drawn out from the camera main body 32 is fixed to the fixing portion 28.

Accordingly, compared with when the fastening portion 44 of the bracket 40 is fixed to the fixing portion 28 without the bracket 40 being temporarily fixed, the position of the bracket 40 (i.e., of the fastening portion 44) on the fixing portion 28 can be stabilized. Accordingly, it is possible to improve workability when screwing the fixing screw 48 into the female threaded portion 28A.

Moreover, because the temporary fixing portion 26 is disposed on the left side of the fixing portion 28, when the fixing screw 48 is being screwed into the female threaded portion 28A (i.e., is being rotated towards the right), force towards the rearward side is applied via the fastening portion 44 to the hook 46. In other words, force is applied to the upper end portion 46A of the hook 46 in the direction in which it is inserted into the slit portion 25. Accordingly, when the fixing screw 48 is being screwed into the female threaded portion 28A, there is little possibility that the upper end portion 46A of the hook 46 will come free from the slit portion 25, and this hook 46 forms a stopper preventing the bracket 40 (i.e., the fastening portion 44) from rotating relative to the fixing portion 28.

Moreover, as is described above, the upper end portion 46A of the hook 46 is caught by the catch portion 27 provided on the lower end portion of the slit portion 25 (in other words, the hook 46 is temporarily fixed to the temporary fixing portion 26) due to the reaction force generated as a result of the lead wire 36, which is extremely rigid (i.e., stiff), being curved when it is drawn out. Accordingly, superior urging force causing the upper end portion 46A of the hook 46 to be caught by the catch portion 27 is obtained.

Furthermore, because urging force is obtained from the reaction force generated by the lead wire 36, there is no need to provide a separate urging mechanism in order to cause the upper end portion 46A of the hook 46 to be caught by the catch portion 27 (i.e., in order to temporarily fix the hook 46 to the temporary fixing portion 26). As a result, compared with when such a separate urging mechanism is provided, both a reduction in the number of parts and a reduction in manufacturing costs can be achieved.

Moreover, in the main body portion 22 (i.e., the front end portion 22B) of the column cover 20, the temporary fixing portion 26 and the fixing portion 28 are placed next to each other and are formed as a single body (i.e., are integrated with each other). Accordingly, compared with when the temporary fixing portion 26 and the fixing portion 28 are formed as mutually independent bodies that are separated from each other, the rigidities of the temporary fixing portion 26 and the fixing portion 28 are improved. Additionally, In the bracket 40, the length in the vehicle width direction of the fastening portion 44, including the hook 46, can be shortened (in other words, the bracket 40 can be made more compact).

Furthermore, the present exemplary embodiment has the excellent advantage that, because the anchoring portion is formed as the hook 46, and the temporary fixing portion 26 has the slit portion 25 into which the upper end portion 46A of the hook 46 is inserted, and the catch portion 27 that catches the upper end portion 46A, a mechanism to temporarily fix the bracket 40 can be easily created. Note that, in the rear wall 26C of the temporary fixing portion 26, instead of providing the slit portion 25 which is elongated in the up-down direction, is it also possible to form a hole portion into which the upper end portion 46A of the hook 46 can be inserted while maintaining a slight gap in the up-down direction between itself and the hole portion.

The mounting structure 10 of a driver monitoring device (i.e., the camera 30) according to the present exemplary embodiment has been described above, however, the mounting structure 10 of a driver monitoring device (i.e., the camera 30) according to the present exemplary embodiment is not limited to the example given here. Various modifications and the like may be made to the present disclosure insofar as they do not depart from the spirit or scope of the present disclosure. For example, it is also possible to employ a structure in which the hook 46 (i.e., the upper end portion 46A) of the bracket 40 does not rely on reaction force generated by the lead wire 36, but is instead temporarily fixed to the temporary fixing portion 26 (i.e., is caught by the catch portion 27) solely by the weight of the bracket 40 to which the connectors 35 and 38 are attached.

It is an object of the present disclosure to provide a mounting structure for a driver monitoring device that, when a supporting component that supports a connector which is attached to a lead wire leading from a driver monitoring device main body is being fixed to a fixing portion of a column cover, enables the position of the supporting component on the fixing portion to be stabilized.

A first aspect of the disclosure is a driver monitoring device mounting structure. The structure includes: a driver monitoring device main body that is attached to a steering column; a supporting component that has an anchoring portion and a fastening portion, and that supports a connector that is attached to a lead wire that is drawn out from the driver monitoring device main body; and a column cover that has a temporary fixing portion to which the anchoring portion is temporarily fixed, and a fixing portion to which the fastening portion is fixed, and that covers the steering column.

According to the first aspect, in a supporting component that supports a connector which is attached to a lead wire leading from a driver monitoring device main body, an anchoring portion is temporarily fixed to a temporary fixing portion, and in this state, a fastening portion is fastened to the fixing portion. Accordingly, compared with when the fastening portion of the supporting component is fixed to the fixing portion without the supporting component being temporarily fixed, the position of the supporting portion (i.e., the fastening portion) on the fixing portion can be stabilized.

A second aspect of the disclosure is the driver monitoring device mounting structure of the first aspect, wherein: the lead wire curves along the steering column, and the anchoring portion is temporarily fixed to the temporary fixing portion by a reaction force generated by the lead wire.

According to the second aspect, the anchoring portion is temporarily fixed to the temporary fixing portion by the reaction force of the lead wire which is curved as it is drawn out. Accordingly, there is no need to provide a separate urging mechanism in order to temporarily fix the anchoring portion to the temporary fixing portion, so that compared with when such a separate urging mechanism is provided, both a reduction in the number of parts and a reduction in manufacturing costs can be achieved.

A third aspect of the disclosure is the driver monitoring device mounting structure of the first aspect, wherein the temporary fixing portion and the fixing portion are formed as a single integrated unit.

According to the third aspect, the temporary fixing portion and the fixing portion are formed as a single integrated unit. Accordingly, compared with when the temporary fixing portion and the fixing portion are formed as separate bodies, the rigidities of the temporary fixing portion and the fixing portion are improved.

A fourth aspect of the disclosure is the driver monitoring device mounting structure of the first aspect, wherein the anchoring portion, a distal end of which is bent into a hook-shape, and the temporary fixing portion has a slit portion or a hole portion, into which the hook-shaped distal end is inserted, and a catch portion that catches the hook-shaped distal end.

According to the fourth aspect, a distal end of the anchoring portion is formed as a bent hook, and the temporary fixing portion has a slit portion or a hole portion into which a distal end of the hook is inserted, and a catch portion that catches the distal end of the hook. Accordingly, a mechanism to temporarily fix the supporting component can be easily created.

According to the present disclosure, when a supporting component that supports a connector which is attached to a lead wire leading from a driver monitoring device main body is being fixed to a fixing portion of a column cover, the position of the supporting component on the fixing portion can be stabilized.

What is claimed is:

1. A driver monitoring device mounting structure, the structure comprising:
   a driver monitoring device main body that is attached to an upper portion of a steering column that supports a steering wheel, the driver monitoring device main body being disposed on the upper portion of the steering column and in front of the steering wheel as viewed in a front-rear direction of a vehicle;
   a supporting component that has an anchoring portion and a fastening portion, and that supports a connector that is attached to a lead wire that is drawn out from the driver monitoring device main body; and
   a column cover that has a temporary fixing portion to which the anchoring portion is temporarily fixed, and a fixing portion to which the fastening portion is fixed,
   wherein the column cover covers the anchoring portion, the fastening portion, the temporary fixing portion and the steering column,
   wherein the anchoring portion is temporarily fixed to the temporary fixing portion by means of a weight of the supporting component.

2. The driver monitoring device mounting structure according to claim 1, wherein:
   the lead wire curves along the steering column, and
   the anchoring portion is temporarily fixed to the temporary fixing portion by a reaction force generated by the lead wire.

3. The driver monitoring device mounting structure according to claim 1, wherein the temporary fixing portion and the fixing portion are formed as a single integrated unit.

4. The driver monitoring device mounting structure according to claim 1, wherein the column cover covers the driver monitoring device main body.

5. A driver monitoring device mounting structure, the structure comprising:
   a driver monitoring device main body that is attached to an upper portion of a steering column that supports a steering wheel, the driver monitoring device main body being disposed on the upper portion of the steering column and in front of the steering wheel as viewed in a front-rear direction of a vehicle;
   a supporting component that has an anchoring portion and a fastening portion, and that supports a connector that is attached to a lead wire that is drawn out from the driver monitoring device main body; and
   a column cover that has a temporary fixing portion to which the anchoring portion is temporarily fixed, and a fixing portion to which the fastening portion is fixed,
   wherein the column cover covers the anchoring portion, the fastening portion, the temporary fixing portion and the steering column, and
   wherein the anchoring portion includes a distal end bent into a hook-shape, and the temporary fixing portion includes (i) a slit portion or a hole portion, into which the hook-shaped distal end is inserted, and (ii) a catch portion that catches the hook-shaped distal end.

* * * * *